United States Patent [19]
Römisch et al.

[11] Patent Number: 5,968,759
[45] Date of Patent: Oct. 19, 1999

[54] METHOD FOR THE QUANTIFICATION OF ACTIVATED COAGULATION FACTOR VII (FVIIA)

[75] Inventors: Jürgen Römisch, Marburg; Hans-Arnold Stöhr, Wetter, both of Germany

[73] Assignee: Centeon Pharma GmbH, Marburg, Germany

[21] Appl. No.: 08/731,580

[22] Filed: Oct. 16, 1996

[30] Foreign Application Priority Data

Oct. 18, 1995 [DE] Germany .................. 195 38 716

[51] Int. Cl.$^6$ .............................. C12Q 1/56; C12Q 1/37; C12Q 1/00
[52] U.S. Cl. .................. 435/13; 435/2; 435/23; 435/4; 435/183; 436/69; 514/56; 514/1; 424/529; 424/530; 424/531; 530/380; 530/381; 536/21
[58] Field of Search .................... 435/13, 2, 23, 435/4, 183, 69; 514/56, 1; 424/530, 531, 529; 530/380, 381; 536/21; 436/69

[56] References Cited

U.S. PATENT DOCUMENTS

| | | | |
|---|---|---|---|
| 3,880,714 | 4/1975 | Babson | 435/13 |
| 4,415,559 | 11/1983 | Suzuki et al. | 435/13 |
| 4,416,812 | 11/1983 | Becker et al. | 435/13 |
| 4,456,591 | 6/1984 | Thomas | 435/13 |
| 5,017,556 | 5/1991 | O'Brien et al. | 514/8 |
| 5,093,237 | 3/1992 | Enomoto | 435/13 |
| 5,118,614 | 6/1992 | Ryback et al. | 435/13 |
| 5,344,918 | 9/1994 | Dazey et al. | 435/13 |
| 5,348,942 | 9/1994 | Little et al. | 435/13 |
| 5,374,617 | 12/1994 | Morrissey et al. | 514/8 |
| 5,472,850 | 12/1995 | Morrissey | 435/13 |

FOREIGN PATENT DOCUMENTS

| | | |
|---|---|---|
| 2045869 | 12/1991 | Canada . |
| 0 346 241 | 12/1989 | European Pat. Off. . |
| 0 464 533 | 1/1992 | European Pat. Off. . |
| 0 464 533 A1 | 1/1992 | European Pat. Off. . |
| 0 547 932 | 6/1993 | European Pat. Off. . |
| WO 92/18870 | 10/1992 | WIPO . |
| WO 94/22905 | 10/1994 | WIPO . |

OTHER PUBLICATIONS

S. Kang et al., "Purification of Human Brain Tissue Factor", Thrombosis and Haemostasis, vol. 59 59(3), pp. 400–403, 1988. Month not available.

A. Johnstone et al., "Affinity Chromatography and Immunoprecipitation", Immunochemistry in Practice, 2$^{nd}$ Ed. Blackwell pub., Chap. 10, pp. 207–219 and 222–224, 1987. Month not available.

L. Rao et al., "Affinity purification of human brain tissue factor utilizing factor VII bound to immobilized anti–factor VII", Anal. Biochem., vol. 165(2), pp. 365–370, 1987. Month not available.

U. Seliqsohn et al., "Coupled Amidolytic Assay for Factor VII: Its Use With a Clotting Assay to Determine the Activity State of Factor VII", Blood 52(5):978–988 (1978). Month not available.

J. Morrissey, "Tissue Factor Modulation of Factor VIIa Activity: Use in Measuring Trace Levels of Factor VIIa in Plasma", Throm. Haemostas. 74(1):185–188 (1995). Month not available.

P. Neuenschwander et al., "Deletion of the Membrane Anchoring Region of Tissue Factor Abolishes Autoactivation of Factor VII but Not Cofactor Function", Biol. Chem, 267(20):14477–14482 (1992). Month not available.

H. Godal et al., "Progressive Inactivation of Purified Factor VII by Heparin and Antithrombin III", Throm. Res., 5:773–775 (1974). Month not available.

Karin et al, "Thrombosis and Haemostasis", vol. 73(3), pp. 429–434, 1995. Month not available.

Kitchen et al, "Thrombosis Research", vol. 50(1), pp. 191–200, 1988. Month not available.

*Primary Examiner*—Louise N. Leary
*Attorney, Agent, or Firm*—Finnegan, Henderson, Farabow, Garrett & Dunner, L.L.P.

[57] ABSTRACT

The invention relates to a method for the quantification of coagulation factor VIIa (F VIIa) in FVIIa- or FVII/FVIIa-containing solutions by means of selective binding to immobilized soluble thromboplastin.

9 Claims, No Drawings

METHOD FOR THE QUANTIFICATION OF ACTIVATED COAGULATION FACTOR VII (FVIIA)

A method for the quantification of activated coagulation factor VII (FVIIa).

The invention relates to a method for the quantification of coagulation factor VIIa (F VIIa) in FVIIa- or F VII/FVIIa-containing solutions by means of selective binding to immobilized soluble thromboplastin.

Coagulation factor VII (FVII) represents, together with thromboplastin (tissue factor, TF), the initiator complex for the extrinsic coagulation pathway. The physiologically active portion of the TF-FVII/TF-FVIIa mixture, namely TF-FVIIa, very efficiently activates factor X (FX to FXa) in the presence of (preferably negatively charged) lipids and calcium. FXa in turn catalyzes (together with FVa, lipids and calcium) the generation of thrombin. The subsequent formation of fibrin (inter alia) ensures wound closure. Results of investigations in recent decades lead to the supposition that elevated FVIIa levels contribute to prothrombotic events and might even be the cause thereof. Correspondingly, (early) detection and quantification of traces of FVIIa in body fluids, especially plasma, is of interest.

Several methods have been described for FVIIa determination: the first method makes use of the fact that traces of FVIIa more efficiently increase the rate of coagulation in appropriate in vitro test systems (for example clotting test in FVII-deficient plasma) than FVII. By contrast, the difference between FVII and FVIIa is far less in a test system based on activation of FX and detection of FXa in the pure system (in the presence of complete TF/lipid and chromogenic FXa substrate)—and this test accordingly indicates the total of FVII/FVIIa. The quotient of the FVII contents found in these tests provides information on the presence of activated FVIIa (Seligsohn et al. Blood 1978; 52: 978–988). Interference with both tests is possible by other activated factors present (for example FIIa, FXa, FIXa), and the results may be falsified. Another described method makes use of the fact that soluble TF (sTF, extracellular domain) induces the fibrin formation by sTF-FVIIa (via FXa, FIIa), but is inert to autoactivation processes of FVII (bound to TF) and activation by FXa (Morrissey; Thromb. Haemostas. 1995; 74:185–188). However, the effect of other activated factors (see above) is unclear.

The abovementioned tests are designed to detect traces of FVIIa in plasma samples but, according to experience to date, are only provisionally suitable for detection thereof in factor concentrates. These products, such as prothrombin complex concentrates or FVII concentrates, are used, for example, for replacement in patients with inborn or acquired deficiencies in coagulation factors. Traces of activated factors, including FVIIa, may lead to thromboembolic complications and death in the patient. It is therefore particularly important to detect and eliminate/block FVIIa. Since the coagulation factors are present in high concentration in the products, selective detection of FVIIa is difficult:

a.) Traces of other activated factors may falsify the test results (see above); b.) the abovementioned systems were designed to test plasma samples; the concentrate used as sample alters, because of the high concentrations of various factors, the conditions by comparison with plasma (in the plasma test system). The suitability for such quantifications has not been proven to date and very probably also does not exist.

The method described by Godal et al. (Thromb. Res. 1974; 5:773–775) makes use of the fact that FVIIa is inhibited by antithrombin (AT) III/heparin in the cold. Estimation of the FVIIa content is possible by coagulometric measurement (in FVII-deficient plasma) of the starting material (without ATIII/heparin) and inhibited solution. However, interference with this method is also possible by the presence of other activated factors. In addition, quantitative inhibition of FVIIa takes place slowly (the sample is normally incubated with ATIII/hep. at 4° C. overnight) and thus entails the risk of additional activations or denaturations during the standing time.

The present invention is therefore based on the object of providing a method for specific quantification of FVIIa which is thus also suitable for detecting FVIIa in plasma concentrates.

The object has been achieved as follows: FVIIa (and FVII) is bound from an FVIIa- or FVII/FVIIa-containing solution on an immobilized sTF, and unbound molecules are removed by washing the solid phase. FVIIa is then quantified a.) directly by addition of a suitable substrate or indirectly by addition of a physiological substrate (factor IX or X) and subsequent determination thereof or b.) by elution of the FVII/FVIIa bound to the immobilized sTF and subsequent determination of the FVIIa. It is possible where appropriate to add to the sample, before contact with the immobilized sTF, a suitable amount of AT III/heparin in order to prevent further formation of FVIIa from FVII (see below). After incubation, the heparin can be neutralized, for example with protamine, and the FVIIa can be detected as described above.

We have found that the use of immobilized sTF makes it possible specifically to quantify FVIIa; this is not possible with complete TF (lipid-containing)—even on immobilization by binding to a solid phase, because autoactivation reactions to TF-FVIIa and activation by FXa do not permit reliable selective measurement.

The coupling (covalently or non-covalently) of sTF to a suitable solid phase (microtiter plate, tube or gel matrices/Sepharose etc.) can take place by generally known methods. In a preferred embodiment, sTF is bound by means of an antibody (PAb; MAb; Fab etc.) against sTF, which is immobilized on the solid phase. Another preferred embodiment provides for the binding of an Fc-sTF fusion protein by means of an anti-Fc or other suitable antibody bound to the solid phase, or protein A or G immobilized on the solid phase. It is therefore expedient for Fc-sTF to be prepared by genetic manipulation as described in European Patent Application EP-A-0 464 533. These preferred embodiments have the advantage that the sTF is presented in a defined form readily accessible to FVII/FVIIa, and the subsequent substrate cleavage takes place appropriately. This association can be converted by suitable methods into a covalent bond. This is particularly important when Fc-sTF is immobilized, and Fc fragment-containing or immunoglobulin-containing samples are tested.

Factor VIIa-containing samples, such as body fluids, especially plasma, or factor concentrates, such as PPSB or FVII products, are brought into contact with the abovementioned immobilized sTF in the presence of calcium and incubated, the sample solution is removed, and the solid phase is washed (where appropriate several times). This procedure removes constituents of the sample (for example activated factors etc.) which potentially interfere with or prevent the reactions described hereinafter, and may falsify the results. FVIIa can be quantified by adding a suitable substrate. In the method described, not only does sTF act as a very selective binding site for FVII and FVIIa (which could, after all, also be done by an appropriate anti-FVII antibody), but it also potentiates (like a cofactor) the amidolytic activity of FVIIa in the presence of calcium. Suitable substrates are customarily used peptide substrates which have chromogenic or fluorogenic groups etc. and whose cleavage can be measured by photometry/fluorimetry. The sensitivity of the test system is increased, and the result is more physiologically relevant, when natural substrates such as FIX and/or FX are added. The presence of calcium and coagulation-promoting lipids considerably increases the rate of activation of FIX and FX and they are therefore added in a preferred method. Addition of substrates which can be cleaved by FIXa or FXa makes quantification thereof—and thus of FVIIa—possible by means of appropriate standard plots. In another preferred embodiment, aliquots of the FIXa or FXa generated in this way can be quantified in an appropriate coagulation test (plasma, deficient plasma). It is furthermore possible to use appropriately other FIXa and FXa substrates of a chemical or biological nature for quantification and/or enhancement of the cascade reaction.

In another preferred procedure, the FVII/FVIIa coupled to the sTF immobilized as described above is eluted by a suitable solution. An agent which complexes doubly charged ions, for example citrate, oxalate or EDTA, is preferably added. The FVII/FVIIa-containing eluate is then tested by the methods described above (where appropriate after addition of calcium, lipids): directly (FVIIa substrate) or indirectly (FX or FIX and suitable substrates or by coagulometry). The FVIIa-containing solution—now free of other interfering (activated) factors—can also be quantified by means of a test which makes use of the selectivity of sTF in respect of the FX activation initiated by sTF/FVIIa, and the next reaction (coagulation). A test of this type can be carried out, for example, as described by Neuenschwander et al. (J. Biol. Chem. 1992; 267: 14477–14482).

Samples which, besides FVIIa, also contain other activated factors (see above) may lead to further generation of FVIIa (where appropriate from the excess of factor VII present) and thus to artificial results. To obviate this risk, it is possible to add antithrombin III/heparin to the sample before contact with the immobilized sTF. Since FVIIa is inhibited only slowly, compared with other potentially interfering factors (FIIa, FIXa, FXa etc.), by ATIII/hep. at room temperature or higher temperatures, the latter factors can be blocked with a negligible effect on the content of FVIIa. TF-bound FVIIa may in some circumstances be inhibited better by ATIII/hep. than the free molecules (but ATIII without functional heparin reacts only very slowly, analogous to soluble FVIIa). It is therefore possible, before contact with sTF, to neutralize the added heparin by means of known reagents such as protamine sulfate/Polybrene®, and then to carry out the method as described above. Likewise suitable for this step in the method are reversible inhibitors, for example benzamidine, and other cofactor-dependent inhibitors which themselves, or their accelerators, are neutralizable (for example heparin-cofactor II/heparin).

In the case of samples which contain FVII and FVIIa there is frequently interest not only in the absolute concentration of FVIIa but also in its proportion of the total FVII/FVIIa content. Activity tests or appropriate antigen detection systems (for example FVII ELISA) are suitable for determining the total FVII content. However, it is practicable during the abovementioned method to quantify the totality of the molecules bound to (and then, where appropriate, eluted from) the solid phase (for example microtiter plate well, tube, gel matrix etc.), and relate it to the FVIIa concentration detected:

The total amount bound can be determined by activation of all sTF-bound FVII molecules (or sTF-FVII) still present as zymogen, and subsequent addition of an abovementioned FVIIa substrate (measurement as described). It is possible to use as activator, for example, thrombin, FXa, FIXa, precallicrein activator, TF/lipid (in each case preferably in the presence of calcium) etc. Before addition of the FVIIa substrate, this activator should be removed by thoroughly washing the solid phase in order to avoid nonspecific/ unwanted substrate reactions. Also suitable are inhibitors which inhibit these activators but do not block the sTF-bound FVIIa. An example which is to be mentioned is thrombin, which can be specifically inhibited by r-hirudin.

In the case of elution of FVII/FVIIa it is advisable to determine the total amount by means of a chromogenic test. The total of FVII and FVIIa can be measured by adding, for example, complete TF/lipid, calcium, FX and a substrate which can be cleaved by FX, incubating and measuring the substrate conversion (Seligsohn et al.; Blood 1978; 52: 978–988).

The invention is illustrated by the following examples.

EXAMPLE 1

Binding of FVII/FVIIa to microtiter plates loaded with Fc-sTF (coated with protein A) and determination of FVIIa Material Microtiter plates coated with protein A (saturation of free valences with an albumin-containing solution and subsequent washing) were loaded with Fc-sTF by incubation at 37° C. for 1 hour, and the plates were washed and used for the FVIIa test. FVIIa of known activity/antigen content highly purified from plasma was used to construct a standard plot.

Binding of FVIIa

One part (for example 50 $\mu$l) of a $CaCl_2$-containing buffer (30 mM) (initial buffer) was introduced into each of the wells of the microtiter plates, and one part of the sample to be determined was pipetted into each. In the case of construction of the standard plots, the sample contained increasing concentrations of FVIIa in the range from 0 to 3000 ng/ml. The initial buffer additionally contained albumin and detergent in order to prevent nonspecific bindings to vessel walls (it is furthermore possible to add to this buffer protamine if the sample contains heparin). After incubation at 37° C. for one hour, the plates were washed several times with a calcium-containing buffer solution.

Measurement of FVIIa activities

A defined volume (100 $\mu$l) of a solution which contained calcium (5 mM $CaCl_2$), coagulation-promoting lipid/lipid mixture (for example Pathromtin®, Behringwerke AG), purified FX (1 IU/ml) and a substrate which can be cleaved by FXa (4 mM S-2222, Chromogenix AB/Sweden) was pipetted into each well of the microtiter plate. To prevent nonspecific substrate cleavages or activation reactions by traces of thrombin (which might be carried over with the FX), 10 $\mu$g/ml r-hirudin (HBW 023, Behringwerke AG/Hoechst AG) were added. After incubation at 37° C. for one hour, the reaction was stopped by adding 100 $\mu$l/well of 10% strength acetic acid, and the $OD_{405}$ was determined by photometry. Control mixtures a) without sample, b) with lipid/substrate/hirudin but without FX, and c) without Fc-sTF were included.

In this example, the standard plot was constructed between 0 and 3000 ng/ml FVIIa. The OD405 after one hour are shown in the following table:

| FVIIa (ng/ml) | OD405 (Means of duplicate determinations) |
| --- | --- |
| 0 | 0 |
| 30 | 0.08 |
| 100 | 0.20 |
| 300 | 0.40 |
| 1000 | 0.73 |
| 3000 | 0.93 |
| Controls a/b/c | 0–0.015 |

EXAMPLE 2

Binding to Fc-sTF coupled to protein A-Sepharose, and elution:
Determination of FVIIa and the total concentrations of FVII/FVIIa Binding and elution of FVII/FVIIa Protein A-Sepharose was loaded with Fc-sTF, and the matrix was washed and used for the binding of FVII/FVIIa.

0.5 ml portions of the (protein A-coated) Sepharose loaded with Fc-sTF were packed into small columns and equilibrated with $CaCl_2$ (5 mM)-containing buffer. The FVII/FVIIa-containing solutions were diluted with $CaCl_2$-containing buffer. 0.5 ml portions of these solutions were loaded onto the column at room temperature. The columns were washed with a $CaCl_2$-containing buffer. Elution took place with a sodium citrate (50 mM)-containing buffer solution.

Quantification of FVIIa and the total concentration of FVII/FVIIa

FVIIa eluted from the abovementioned matrix was quantified using a test system described by Neuenschwander et al. (J. Biol. Chem. 1992; 267: 14477–14482): various sample dilutions were mixed with an FVII-deficient plasma. The time until coagulation occurred in the presence of sTF, lipid and calcium was determined using a Schnitger and Gross coagulometer, and the FVIIa contents were determined by means of a standard plot. A standard plot was constructed using increasing concentrations of rFVIIa from NIBSC (UK).

The total FVII/FVIIa contents were determined by a modification of the method of Seligsohn et al. (see above): various dilutions of the samples were incubated with complete TF/lipid mixture, calcium and FX. The generation of FXa was stopped after incubation for 3 min by adding EDTA, and the ΔOD/min (chromogenic substrate S-2765; Chromogenix AB) was determined. The references used were increasing concentrations of FVII and FVIIa, on the basis of which the sample contents were determined.

Mixtures

F VII was adjusted to 0.5 U/ml (according to total test) with calcium-containing buffer solution (see Tab. 2: SM=starting material). Other samples with increasing FVIIa contents were prepared, adjusting the FVII+FVIIa concentrations to 0.5 U/ml (according to total test).

Result

As shown in Tab. 2, in each case about 90% of the applied total FVII/FVIIa activities and FVIIa activities (based on the initial quantities) were recovered in the eluates from the sTF columns. Since the aim of the investigations was to determine the FVIIa proportion in the total concentration of a sample containing FVII and FVIIa (expressed as the ratio FVIIa:total FVII/VIIa), the absolute quantities of the factors recovered are immaterial as long as detectability is ensured. As is clear from the factors FVIIa:total FVII/VIIa listed in the table (column 3), this affinity chromatography does not lead to activation of the FVII content (through FVIIa triggering)—which is an important prerequisite for the functioning of this test system.

Even the supposedly pure FVII contains a detectable amount of FVIIa, as shown in Tab. 2 (*).

On successive reduction in the FVII content and replacement by FVIIa, the FVII+VIIa total remained constant in the total test but, as expected, increased in the FVIIa test. Correspondingly, the factor FVIIa: total FVII+VIIa increased with the increase in the FVIIa content. Comparison of these factors, namely SM to eluate, was identical (within the range of variations in the tests) for each of the various mixtures and showed the reliability of the test system.

TABLE 2

| FVIIa content in FVII/VIIa | Total test (U FVII +VIIa/ ml) | | FVIIa test (U FVIIa/ml) | | FVIIa: Tot. (FVIIa U/total U) | |
| --- | --- | --- | --- | --- | --- | --- |
| (%) | SM | Elute | SM | Elute | SM | Elute |
| 0 | 0.50 | 0.39 | 0.07* | 0.050 | 0.14 | 0.13 |
| 2 | 0.55 | 0.39 | 0.30 | 0.225 | 0.55 | 0.58 |
| 5 | 0.50 | 0.38 | 0.62 | 0.488 | 1.24 | 1.28 |
| 20 | 0.55 | 0.42 | 2.38 | 1.820 | 4.33 | 4.33 |
| 100 | 0.50 | 0.35 | 10.15 | 6.500 | 20.30 | 18.57 |

We claim:

1. A method for the detection of activated factor VII (FVIIa) in protein solutions without promoting autoactivation of FVII, comprising
   a) binding the FVIIa to immobilized soluble thromboplastin (sTF)
   b) detecting the amount of bound or eluted FVIIa.

2. The method as claimed in claim 1, wherein, before the binding to immobilized soluble thromboplastin, the starting material is incubated with a combination of antithrombin and heparin and subsequently the heparin is neutralized.

3. The method as claimed in claim 1, wherein a protein A column is used for the sTF-Fc binding.

4. The method as claimed in claim 1, wherein the FVIIa activity is determined by amidolysis.

5. The method as claimed in claim 1, wherein the amount of FVIIa is determined via measuring the generation of FXa or FIXa.

6. The method as claimed in claim 1, wherein the amount of FVIIa is quantified by coagulometry with the aid of a dissolved soluble thromboplastin.

7. The method as claimed in claim 1, wherein the amount of FVIIa is determined by measuring the clotting activity/ total activity ratio.

8. The method as claimed in claim 5, wherein the amount of FVIIa is determined via measuring the generation of FXa and FIXa.

9. The method as claimed in claims 1 or 2, wherein the immobilized soluble thromboplastin is prepared by:
   a) making sTF-Fc by a recombinant method, and
   b) immobilizing said sTF-Fc to a column which binds Fc.

* * * * *